(12) United States Patent
Mägerlein et al.

(10) Patent No.: US 8,003,830 B2
(45) Date of Patent: Aug. 23, 2011

(54) METHOD FOR IMPROVING THE COLOR NUMBER OF TRIMETHYLOLPROPANE

(75) Inventors: Wolfgang Mägerlein, Mannheim (DE); Ulrich Notheis, Dormagen (DE); Michael Friederich, Krefeld (DE); Hans-Dieter Gerriets, Duisburg (DE); Heinrich Grizinia, Erkelenz (DE); Paul Wagner, Düsseldorf (DE)

(73) Assignee: LANXESS Deutschland GmbH, Leverkusen, DE (US)

( * ) Notice: Subject to any disclaimer, the term of this patent is extended or adjusted under 35 U.S.C. 154(b) by 0 days.

(21) Appl. No.: 12/532,174

(22) PCT Filed: Mar. 20, 2008

(86) PCT No.: PCT/EP2008/053376
§ 371 (c)(1),
(2), (4) Date: Jan. 11, 2010

(87) PCT Pub. No.: WO2008/116826
PCT Pub. Date: Oct. 2, 2008

(65) Prior Publication Data
US 2010/0137656 A1    Jun. 3, 2010

(30) Foreign Application Priority Data
Mar. 23, 2007  (DE) .................. 10 2007 013 963

(51) Int. Cl.
*C07C 31/18* (2006.01)
(52) U.S. Cl. ................................................ 568/853
(58) Field of Classification Search .................. 568/853
See application file for complete search history.

(56) References Cited

U.S. PATENT DOCUMENTS

| | | | | |
|---|---|---|---|---|
| 3,037,060 A | 5/1962 | Dege | ............................ | 260/637 |
| 3,097,245 A | 7/1963 | Russell et al. | ................ | 260/635 |
| 5,603,835 A | 2/1997 | Cheung et al. | ................ | 210/639 |
| 6,586,642 B2 | 7/2003 | Dernbach et al. | ............. | 568/854 |
| 7,057,080 B2 * | 6/2006 | Dernbach et al. | ............. | 568/700 |
| 2004/0225162 A1 | 11/2004 | Sunkara et al. | ............... | 568/852 |

FOREIGN PATENT DOCUMENTS

| | | |
|---|---|---|
| CS | 184381 | 7/1980 |
| DE | 10029055 | 1/2002 |
| SU | 125552 | 5/1959 |

OTHER PUBLICATIONS

International Search Report; co-pending Application No. PCT/EP2008/053376, dated Jul. 8, 2008.
H. Moureu, et al., Mem. Poudres 32, 89 (1950).
Org. Synth., Collect, vol. 1, 425, 1950.

* cited by examiner

*Primary Examiner* — Sikarl Witherspoon
(74) *Attorney, Agent, or Firm* — Michael A. Miller

(57) ABSTRACT

The present invention relates to a method for the production of trimethylolpropane with a low color number by treatment with activated carbon.

6 Claims, No Drawings

METHOD FOR IMPROVING THE COLOR NUMBER OF TRIMETHYLOLPROPANE

The present invention relates to a method of producing trimethylolpropane having a low color number by treatment with activated carbon.

Trimethylolpropane, hereinafter referred to as TMP, is widely used industrially for producing polyesters, polyurethanes, polyethers, polymer foams, plasticizers, alkyd resins, protective paints, lubricants, textile finishes and elastomers. Furthermore, it replaces glycerol in some industrial applications.

On an industrial scale, TMP is prepared predominantly by two alternative processes.

The inorganic Cannizzaro process comprises firstly aldol condensation of butanal and formaldehyde in the first step and, in a second step, crossed Cannizzaro reaction between the aldol condensation product of the first step and formaldehyde in the presence of stoichiometric amounts of an inorganic base such as sodium hydroxide or calcium hydroxide. The dimethylolbutanal formed as aldol condensation product in the first step reacts in the second step with excess formaldehyde in a disproportionation reaction to form TMP and, depending on the base used, the corresponding formate, for example sodium formate or calcium formate. In a modification, viz. the organic Cannizzaro process, a tertiary alkylamine is used instead of an inorganic base in the second step. This usually enables higher yields to be achieved compared to when an inorganic base is used. Trialkylammonium formate is obtained as by-product.

Furthermore, TMP can be prepared by the hydrogenation process. Here, formaldehyde is reacted with butanal in the presence of catalytic amounts of an amine to form dimethylolbutanal. After the removal of excess formaldehyde, the reaction mixture is subjected to a hydrogenation in which the desired TMP is obtained.

Commercially available TMP grades usually have a color caused by the presence of impurities. However, in some applications, for example the production of particularly transparent polyesters or particular surface coating raw materials, this color is undesirable. The literature describes various methods by means of which an improvement in the color number of TMP is said to be achieved.

U.S. Pat. No. 3,097,245 describes a process for preparing TMP having an APHA color number in the range from 50 to 200. This color number is achieved by adhering to particular reaction conditions in respect of temperature, reaction time, pH and concentration of the starting compounds in the Cannizarro reaction. Furthermore, the reaction is followed by treatment of the resulting solution with an ion-exchange resin.

U.S. Pat. No. 5,603,835 discloses a process for preparing TMP having APHA color numbers of less than 100 by extractive after-treatment of crude TMP solutions with an ether or an ester.

Both the above-described methods of improving the color number of TMP have the disadvantage that they are technically complicated since particular conditions have to be adhered to precisely and additionally require the use of an ion-exchange resin or the introduction of at least one solvent.

SU-A 125552 describes a hydrogenation for the purification of TMP which has been prepared by the Cannizzaro process. TMP having a content of about 98% is obtained by hydrogenation over nickel, zinc, molybdenum or copper catalysts and subsequent distillation. It is mentioned that the TMP obtained is colorless, but no color number is reported. However, it has been found in practice that the color number which can be obtained by this process is not satisfactory for many purposes.

A further method of improving the color number of TMP by hydrogenation is described in the patent application DE 199 63 442. Here, TMP is purified by distillation after it has been prepared and is subsequently preferably treated with a heterogeneous catalyst under hydrogen pressure. The color number achieved by hydrogenation can be improved further by prior multiple distillation.

However, disadvantages of all hydrogenation processes for improving the color number are the high outlay in terms of apparatus and a reduction in quality of the TMP obtained as a result of catalyst abrasion. Furthermore, the costs of the catalyst reduce the economic efficiency.

DE 100 29 055 describes a method of improving the color number of TMP in which the TMP which has been prepurified by distillation and has a purity of preferably >95% is subjected to a heat treatment, preferably at temperatures of from 160 to 240° C., and the TMP is subsequently repurified, preferably by distillation. The heat treatment step converts the color-imparting secondary components into high-boiling, relatively nonvolatile components. However, this method has the disadvantage that the heat treatment has to be followed by another purification step, for example a distillation, or this purification step has to be coupled with the heat treatment in order to remove these high-boiling secondary components and to obtain a TMP having a low color number.

A further method of improving the color number of polyalcohols uses activated carbon for removing the impurities. A corresponding process for pentaerythritol is described, for example, in H. Mouren et al., Mem. Poudres 32, 89 (1950) and Org. Synth., Collect, Vol. 1, 425.

In CZ 184381, oxidants and/or reducing agents such as potassium permanganate and sodium sulfite are used for purifying TMP and other polyalcohols, preferably in the presence of activated carbon or other materials which can bind the impurities. APHA color numbers of > about 100 are achieved.

However, the methods mentioned have the disadvantage that they are carried out in dilute solutions, which is uneconomical due to the necessity of separating the solvent from the product.

It is therefore an object of the invention to provide an efficient method of producing TMP having a low color number which can be carried out without complicated apparatuses and overcomes the disadvantages of the prior art.

A method of producing TMP, which is characterized in that essentially pure, liquid TMP is brought into contact with activated carbon and the activated carbon is subsequently separated off, has now been found.

Here, essentially pure means that the TMP content of the substance which is brought into contact with the activated carbon is from 80 to 100% by weight, preferably from 90 to 100% by weight, particularly preferably from 94% by weight to 100% by weight and very particularly preferably from 98.00 to 99.99% by weight.

Preference is given to using TMP which has been distilled before being used in the method of the invention.

For the purposes of the present invention, liquid means that the substance which is brought into contact with the activated carbon contains less than 5% by weight, preferably less than 1% by weight, of solids. Solids can be, for example, unmelted TMP or other solid materials.

To achieve the liquid state, preference is given to conditions in which, firstly, the dynamic viscosity of the TMP has values which allow industrial processing such as pumping, stirring, etc., to be carried out essentially without problems.

Preference is given to a dynamic viscosity range from 2.4 to 160 cP, particularly preferably a dynamic viscosity range from 11 to 62 cP. At ambient pressure, this corresponds to a temperature range from 80 to 200° C., preferably from 100 to 150° C., particularly preferably from 100 to 120° C. The use of superatmospheric pressure is in principle also possible.

The method of the invention can be carried out batchwise or continuously.

To carry out the method batchwise, it is possible, for example, to melt TMP, and mix the melt with a particular amount of activated carbon and, after a particular contact time, finally remove the liquid TMP from the activated carbon again.

Sufficient mixing, e.g. by means of stirring, is preferably ensured during contacting. The activated carbon can be separated off by, for example, filtration, centrifugation or sedimentation.

To carry out the method continuously, it is possible, for example, to pump liquid TMP through a bed of activated carbon in a single pass or with circulation. Here, it is possible to employ, for example, a downflow mode or an upflow mode. In a preferred embodiment, particulate activated carbons are used as fixed beds.

In one embodiment, the TMP flows into the activated carbon from below and, during start-up, the first part of the product stream which still contains activated carbon particles is recirculated or discarded. After some time, clear product is then obtained. When the decolorization capacity of the activated carbon is exhausted, the activated carbon can be regenerated or replaced. The regeneration can be carried out, fore example, by thermal treatment or by treatment with steam.

In a further embodiment, the liquid TMP is passed through a number of activated carbon beds connected in series in such a way that one or more beds are utilized for purification while at the same time at least one activated carbon bed is regenerated. The beds are in this way regenerated in order. The regeneration of the beds can, for example, be effected by allowing the liquid TMP to drain from the bed and subsequently treating the activated carbon with steam.

As activated carbons, it is in principle possible to use all known activated carbons. Preferred activated carbons are those which are produced from wood charcoal, brown coal, hard coal, peat, wood, coconut shells or olive stones.

The activated carbons can have been produced by steam activation or by chemical activation, with further treatment steps such as washing, pH modification, impregnation, heat treatment or oxidation or reduction or various shaping processes such as granulation, extrusion or pelletization optionally being able to be carried out.

The habit of the activated carbons is in principle not restricted for use in the method of the invention. Preference is given to using pulverulent, particulate, granulated or extruded activated carbons.

In one embodiment of the invention, activated carbons which have a pH (aqueous extract) in the range from 1 to 12 under standard conditions are used. Preference is given to activated carbons which have a pH in the range from 4 to 9 under standard conditions.

Furthermore, the activated carbons used can, for example, have BET surface areas in the range from 500 to 2500 $m^2/g$. Preference is given to activated carbons which have BET surface areas in the range from 700 to 2000 $m^2/g$.

In a preferred embodiment, the method of the invention is employed at a point in the production process at which the TMP is present in molten form, for example after purification by distillation.

The contacting of the essentially pure TMP with activated carbon can, for example, take more than 30 s, preferably from 1 min to 24 h. Particular preference is given to contact times of from 10 min to 8 h, very particularly preferably from 10 min to 4 h.

When the method is carried out batchwise, the amount of activated carbon based on TMP used can be, for example, in the range from 0.01% by weight to 100% by weight. Preference is given to an amount of activated carbon of from 0.1% by weight to 5% by weight.

When the method is carried out continuously, the WHSV is, for example, in the range from 0.01 kg/(l*h) to 10 kg/(l*h), preferably in the range from 0.1 kg/(l*h) to 3 kg/(l*h).

The method of the invention for improving the color number of TMP by means of activated carbon can in principle be employed for TMP from any source. It is possible to use TMP which has been prepared by the organic Cannizzaro process, the inorganic Cannizzaro process or the hydrogenation process. Preference is given to using TMP which has been prepared by an inorganic Cannizzaro process. TMP which has been prepared by the abovementioned methods and has, if appropriate, been subjected to further purification steps typically has initial APHA color numbers of from 10 to 1000.

The method of the invention is characterized by the APHA color number of TMP being able to be improved considerably in an efficient manner.

EXAMPLES

General

The APHA color numbers [classification of the color according to the platinum-cobalt scale, cf. DIN ISO 6271] were determined using a Lico 200 photometer from Dr. Lange. For this purpose, 4-5 g of TMP were in each case placed in an 11 mm round cell, the round cell was closed with a silicone stopper, the TMP was melted at 100° C. and measured. Two measurements were carried out for each sample and the values were averaged.

Example 1

150 g of TMP having a content of 94.47% (GC-% by area) and an APHA color number of 243 were melted and brought to a temperature of 100° C. This was followed by addition of 0.75 g of activated carbon and stirring of the mixture at this temperature for 60 minutes. The mixture was subsequently filtered hot through a heated pressure filter and the APHA color number was determined. The results for various activated carbons are shown in the following table:

| Activated carbon | APHA color number after activated carbon treatment |
|---|---|
| Steam-activated, acid-washed activated carbon extrudate having a BET surface area of 1370 $m^2/g$ and an ash content of 3% by weight (Norit RX 3) | 144 |
| Steam-activated, acid-washed 0.4-2 mm activated carbon granules composed of carbon having a BET surface area of 1125 $m^2/g$, an iodine number of 1025, a methylene blue absorption of 22 g/100 g and an ash content of 0.5% by weight. The aqueous slurry is neutral (Norit GAC 1240+) | 97 |

-continued

| Activated carbon | APHA color number after activated carbon treatment |
|---|---|
| Steam-activated, acid-washed 25μ activated carbon powder having a BET surface area of 1000 m²/g, an iodine number of 250, a methylene blue absorption of 18 g/100 g, a molasses number of 900 [EUR] and an ash content of 4% by weight. The aqueous slurry is neutral (Norit SX 1 G) | 22 |
| Steam-activated, acid-washed 20μ activated carbon powder having a BET surface area of 1100 m²/g, an iodine number of 1050, a methylene blue absorption of 22 g/100 g, a molasses number of 225 [EUR] and an ash content of 5% by weight. The aqueous slurry is neutral (Norit SX 1 G) | 23 |
| Steam-activated, acid-washed 0.8 mm activated carbon extrudate having a BET surface area of 1100 m²/g, an iodine number of 1000, a methylene blue absorption of 22 g/100 g, a molasses number of 350 [EUR] and an ash content of 5% by weight. The aqueous slurry is neutral (Norit Rox 0.8) | 116 |
| Chemically activated, acid-washed, 3 mm particulate activated carbon with an addition of bentonite and having a BET surface area of 1100 m²/g, a methylene blue absorption of 25 g/100 g, a molasses number of 350 [EUR] and an ash content of 15% by weight. The aqueous slurry is acidic (pH 2-3.5) (Norit Bentonorit CA 1) | 52 |

Example 2

150 g of TMP having a content of 99.23% (GC-% by area) and an APHA color number of 10 were melted and brought to a temperature of 100° C. This was followed by addition of 0.75 g of activated carbon and stirring of the mixture at this temperature for 60 minutes. The mixture was subsequently filtered hot through a heated pressure filter and the APHA color number was determined. The results for various activated carbons are shown in the following table:

| Activated carbon | APHA color number after activated carbon treatment |
|---|---|
| Steam-activated, acid-washed activated carbon granules (0.4-2 mm) composed of carbon having a BET surface area of 1125 m²/g, an iodine number of 1025, a methylene blue absorption of 22 g/100 g and an ash content of 0.5% by weight. The aqueous slurry is neutral (Norit GAC 1240+) | 0 |
| Steam-activated, acid-washed activated carbon powder (25μ) having a BET surface area of 1000 m²/g, an iodine number of 250, a methylene blue absorption of 18 g/100 g, a molasses number of 900 [EUR] and an ash content of 4% by weight. The aqueous slurry is neutral (Norit SX 1 C) | 0 |
| Steam-activated, acid-washed 20μ activated carbon powder having a BET surface area of 1100 m²/g, an iodine number of 1050, a methylene blue absorption of 22 g/100 g, a molasses number of 225 [EUR] and an ash content of 5% by weight. The aqueous slurry is neutral (Norit SX Plus) | 0 |
| Steam-activated, acid-washed 0.8 mm activated carbon extrudate having a BET surface area of 1100 m²/g, an iodine number of 1000, a methylene blue absorption of 22 g/100 g, a molasses number of 350 [EUR] and an ash content of 5% by weight. The aqueous slurry is neutral (Norit Rox 0.8) | 3 |
| Chemically activated, acid-washed, 3 mm particulate activated carbon with an addition of bentonite and having a BET surface area of 1100 m²/g, a methylene blue absorption of 25 g/100 g, a molasses number of 350 [EUR] and an ash content of 15% by weight. The aqueous slurry is acidic (pH 2-3.5) (Norit Bentonorit CA 1) | 3 |

Example 3

In two experiments, 70 g of TMP having a content of 99.23% (GC-% by area) and an APHA color number of 10 were in each case melted and brought to a temperature of 100° C. This was in each case followed by addition of 0.35 g of a steam-activated, acid-washed 0.8 mm activated carbon extrudate having a BET surface area of 1100 m²/g, an iodine number of 1000, a methylene blue absorption of 22 g/100 g, a molasses number of 350 [EUR] and an ash content of 5% by weight and giving a neutral aqueous slurry and stirring of the mixture at this temperature for 10 minutes in a first experiment and for 40 minutes in a second experiment. In each case, the mixture was subsequently filtered hot through a heated pressure filter and the APHA color number was determined.

In the experiment with a contact time of 10 min, an APHA color number of the activated carbon-treated TMP of 0 was measured.

In the experiment with a contact time of 40 min, an APHA color number of the activated carbon-treated TMP of 6 was measured.

Example 4

310.5 g of a steam-activated, acid-washed 0.8 mm activated carbon extrudate having a BET surface area of 1100 m²/g, an iodine number of 1000, a methylene blue absorption of 22 g/100 g, a molasses number of 350 [EUR] and an ash content of 5% by weight and giving a neutral aqueous slurry was introduced into a vertical glass tube reactor. TMP from a reservoir maintained at 120° C. was pumped in a single pass through this activated carbon bed from the bottom upward. The WHSV was 0.76 kg/(l*h). The residence time in the activated carbon bed was 55 min. The reactor was maintained at 120° C., and the temperature at the reactor outlet was likewise 120° C. The APHA color number of the TMP collected after passage through the activated carbon bed was measured at set intervals.

The APHA color number of the first TMP overflow after commencement of the experiment was 0. After 3 h in single-pass operation, an APHA color number of 7 was measured. After 5.25 h of single-pass operation, an APHA color number of 3 was measured.

Example 5

Long-Term Experiment

A bed (500 mm height) of steatite spheres (1 mm) was introduced into a tube reactor (38 mm internal diameter, length 800 mm). Above this, a 180 mm high layer of 76.5 g of a steam-activated, acid-washed 0.8 mm activated carbon extrudate having a BET surface area of 1100 m²/g an iodine number of 1000, a methylene blue absorption of 22 g/100 g, a molasses number of 350 [EUR] and an ash content of 5% by weight and giving a neutral aqueous slurry was introduced. TMP from a reservoir maintained at 120° C. was pumped in a single pass through this bed from the bottom upward. The color number of the TMP in the reservoir was 22. The WHSV through the activated carbon was 1.0 kg/(l*h). The residence time in the activated carbon bed was 42 min. The reactor was maintained at 120° C., and the temperature at the reactor outlet was likewise 120° C. The APHA color number of the TMP collected after passage through the activated carbon bed was determined at fixed intervals; the values reported here are averages of three experiments. The results are shown in the following table:

| Time [h] | TMP after purification [APHA color number] |
| --- | --- |
| 0 | 2 |
| 1 | 6 |
| 3 | 7 |
| 4 | 6 |
| 28 | 7 |
| 37 | 8 |
| 48 | 10 |
| 52 | 8 |
| 77 | 11 |
| 95 | 7 |
| 101 | 6 |
| 113 | 11 |
| 119 | 7 |
| 137 | 10 |

-continued

| Time [h] | TMP after purification [APHA color number] |
| --- | --- |
| 164 | 10 |
| 172 | 8 |
| 196 | 8 |

The invention claimed is:

1. A method of producing trimethylolpropane having a low color number, comprising: contacting essentially pure, liquid TMP with activated carbon and separating off the activated carbon, wherein the activated carbon has a BET surface area from 500 to 2500 m$^2$/g.

2. The method as claimed in claim 1, wherein the essentially pure trimethylolpropane has a trimethylolpropane content of from 90 to 100% by weight.

3. The method as claimed in claim 1, wherein the process is carried out at from 80 to 200° C.

4. The method as claimed in claim 1, wherein the activated carbons are those selected from the group consisting of wood charcoal, brown coal, hard coal, peat, wood, coconut shells and olive stones.

5. The method according to claim 1, wherein the contacting of the essentially pure trimethylolpropane with activated carbon takes from 1 min to 24 h.

6. A method of producing trimethylolpropane having a low color number, comprising: contacting essentially pure, liquid TMP with a plurality of activated carbon beds wherein, at least one carbon bed is regenerated after contact with the essentially pure, liquid TMP.

* * * * *